(12) United States Patent
Thomas et al.

(10) Patent No.: US 10,899,510 B2
(45) Date of Patent: Jan. 26, 2021

(54) VIAL ASSEMBLY WITH CAP WITH DISINFECTANT AND RELATED METHODS

(71) Applicants: Nicole Thomas, Apopka, FL (US); Ashley Tilton, Orlando, FL (US)

(72) Inventors: Nicole Thomas, Apopka, FL (US); Ashley Tilton, Orlando, FL (US)

( * ) Notice: Subject to any disclaimer, the term of this patent is extended or adjusted under 35 U.S.C. 154(b) by 349 days.

(21) Appl. No.: 16/162,573

(22) Filed: Oct. 17, 2018

(65) Prior Publication Data

US 2020/0122906 A1   Apr. 23, 2020

(51) Int. Cl.
| | |
|---|---|
| *B65D 51/00* | (2006.01) |
| *A61J 1/14* | (2006.01) |
| *A61L 2/18* | (2006.01) |
| *A61J 1/20* | (2006.01) |
| *B65D 23/00* | (2006.01) |

(52) U.S. Cl.
CPC .......... *B65D 51/002* (2013.01); *A61J 1/1406* (2013.01); *A61J 1/1468* (2015.05); *A61J 1/20* (2013.01); *A61L 2/18* (2013.01); *B65D 23/001* (2013.01)

(58) Field of Classification Search
CPC .......... A61J 1/1468; A61J 1/1406; A61J 1/20; A61L 2/18; B65D 51/002; B65D 51/2835; B65D 51/2828; B65D 23/001
See application file for complete search history.

(56) References Cited

U.S. PATENT DOCUMENTS

| | | |
|---|---|---|
| 4,524,809 A | 6/1985 | Dent |
| 5,014,869 A | 5/1991 | Hammond |
| 5,141,133 A | 8/1992 | Ninomiya et al. |
| 5,366,114 A | 11/1994 | Bernstein et al. |
| 5,554,135 A | 9/1996 | Menyhay |
| 5,694,978 A | 12/1997 | Heilmann et al. |
| 7,971,739 B2 | 7/2011 | Ammann |
| 8,714,380 B2 | 5/2014 | Casale et al. |
| 8,999,073 B2 | 4/2015 | Rogers et al. |
| 9,045,261 B2 | 6/2015 | Chawla et al. |
| 9,192,443 B2 | 11/2015 | Tennican |

(Continued)

OTHER PUBLICATIONS

Baniasadi et al. "Microbial contamination of single- and multiple-dose vials after opening in a pulmonary teaching hospital" BRAZ] Infect Dis . Available online Jan. 5, 2013: 2013 ;17(1):69-73.

(Continued)

*Primary Examiner* — Ariana Zimbouski
(74) *Attorney, Agent, or Firm* — Allen, Dyer, Doppelt + Gilchrist, PA

(57) ABSTRACT

A vial assembly may include a vial having a body to hold a liquid material, and a neck extending from the body. The neck may include a multi-use surface configured to permit access to the liquid material. The vial assembly may include a cap to be received by the neck and to cover the multi-use surface. The cap may include a base having a first major surface, and a second major surface opposite of the first major surface, arms extending from the second major surface, and a rupturable reservoir of disinfectant material carried by the base between the first major surface and the second major surface. One or more of the first major surface and the second major surface may be flexible so as to rupture the rupturable reservoir when the cap is received by the neck.

20 Claims, 10 Drawing Sheets

(56) References Cited

U.S. PATENT DOCUMENTS

| | | | |
|---|---|---|---|
| 9,440,062 B2 | 9/2016 | Adams et al. | |
| 9,498,614 B2 | 11/2016 | Alpert | |
| 9,814,650 B1* | 11/2017 | Dailey | A61J 1/18 |
| 2008/0290061 A1* | 11/2008 | Seelhofer | B65D 51/2835 |
| | | | 215/249 |
| 2009/0216213 A1* | 8/2009 | Muir | B65D 1/09 |
| | | | 604/414 |
| 2011/0174642 A1* | 7/2011 | Coon | B65D 51/2835 |
| | | | 206/222 |
| 2014/0048430 A1* | 2/2014 | Giraud | B65D 43/0235 |
| | | | 206/222 |
| 2017/0015476 A1* | 1/2017 | McClellan | B65D 51/18 |
| 2019/0047756 A1* | 2/2019 | Brandenstein | A61J 1/065 |

OTHER PUBLICATIONS

McKee et al. "The Misuse of Vials Follow-up to the Sentinel Event Alert" Webinar Sep. 11, 2014; https://www.jointcommission.org/assets/1/6/Transcript_Vials_Webinar_9_11_14; 1 pg.

Anonymous Q&A: Vial flip caps' https://infusionnurse.org/2016/02; Feb. 2016; pp. 2.

* cited by examiner

VIAL ASSEMBLY WITH CAP WITH DISINFECTANT AND RELATED METHODS

TECHNICAL FIELD

The present disclosure relates to the field of medical devices, and, more particularly, to a drug vial and related methods.

BACKGROUND

A vial is a small container used to store medication in the form of liquids, capsules, or powder. In the healthcare environment, due to the scale of use, multi-dose vials are used. In typical deployment, the multi-dose vials are stored in a cart or a secure cabinet. When a dose is needed, the multi-dose vial is retrieved, and a dose is extracted. Once the dose has been given to the patient, the multi-dose vial is returned to storage.

One example of the multi-dose vial is the crimp top vial with a rubber insert. This approach is used for liquid and powder medications. To extract the dose, a needle of a syringe is inserted through the rubber insert, and the syringe extracts the needed dose. Once the dose has been extracted, the needle is removed, and the multi-dose vial is returned to storage.

SUMMARY

Generally, a vial assembly may include a vial comprising a body to hold a liquid material, and a neck extending from the body. The neck may include a multi-use surface configured to permit access to the liquid material. The vial assembly may comprise a cap to be received by the neck and to cover the multi-use surface. The cap may include a base having a first major surface, and a second major surface opposite of the first major surface, a plurality of arms extending from the second major surface, and a rupturable reservoir of disinfectant material carried by the base between the first major surface and the second major surface. At least one of the first major surface and the second major surface may be flexible so as to rupture the rupturable reservoir when the cap is received by the neck. Advantageously, the cap is disposable and the multi-use surface may be kept sterile.

In particular, the second major surface may comprise a plurality of flexible lateral supports defining gaps therebetween. Each of the plurality of flexible lateral supports may comprise a distal protrusion extending transversely. In some embodiments, each of the plurality of flexible lateral supports may be circular segment-shaped.

Additionally, each of the plurality of arms may comprise an L-shaped distal end portion for abutting and retaining the neck. Each of the plurality of arms may extend substantially perpendicular to the second major surface. For example, the rupturable reservoir may comprise a foil material body carrying the disinfectant material therein. The first major surface may comprise a plurality of ridges. The base may comprise a circle-shaped base with a flanged annular edge.

Another aspect is directed to a cap to be used with a vial comprising a body to hold a liquid material, and a neck extending from the body. The neck may include a multi-use surface configured to permit access to the liquid material. The cap may be received by the neck and may cover the multi-use surface. The cap may include a base having a first major surface, and a second major surface opposite of the first major surface, a plurality of arms extending from the second major surface, and a rupturable reservoir of disinfectant material carried by the base between the first major surface and the second major surface. At least one of the first major surface and the second major surface may be flexible so as to rupture the rupturable reservoir when the cap is received by the neck.

Yet another aspect is directed to a method for making a cap to be used with a vial comprising a body to hold a liquid material, and a neck extending from the body. The neck may include a multi-use surface configured to permit access to the liquid material. The cap is to be received by the neck and to cover the multi-use surface. The method may comprise forming a base having a first major surface, and a second major surface opposite of the first major surface, forming a plurality of arms extending from the second major surface, and positioning a rupturable reservoir of disinfectant material carried by the base between the first major surface and the second major surface. At least one of the first major surface and the second major surface may be flexible so as to rupture the rupturable reservoir when the cap is received by the neck.

DETAILED DESCRIPTION

Figure 1:
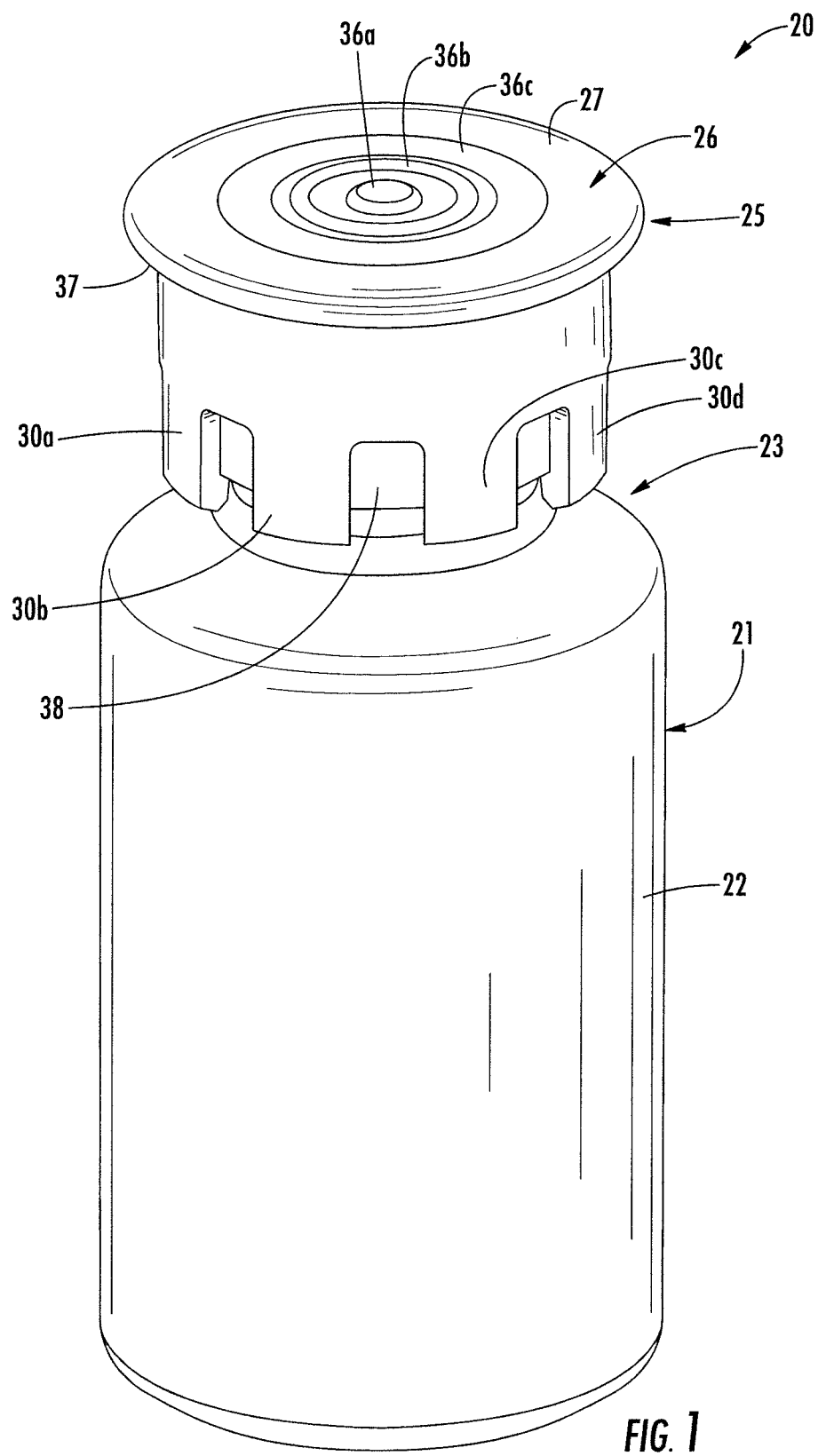
FIG. 1 is a schematic perspective view of a vial assembly, according to the present disclosure.
Figure 2:
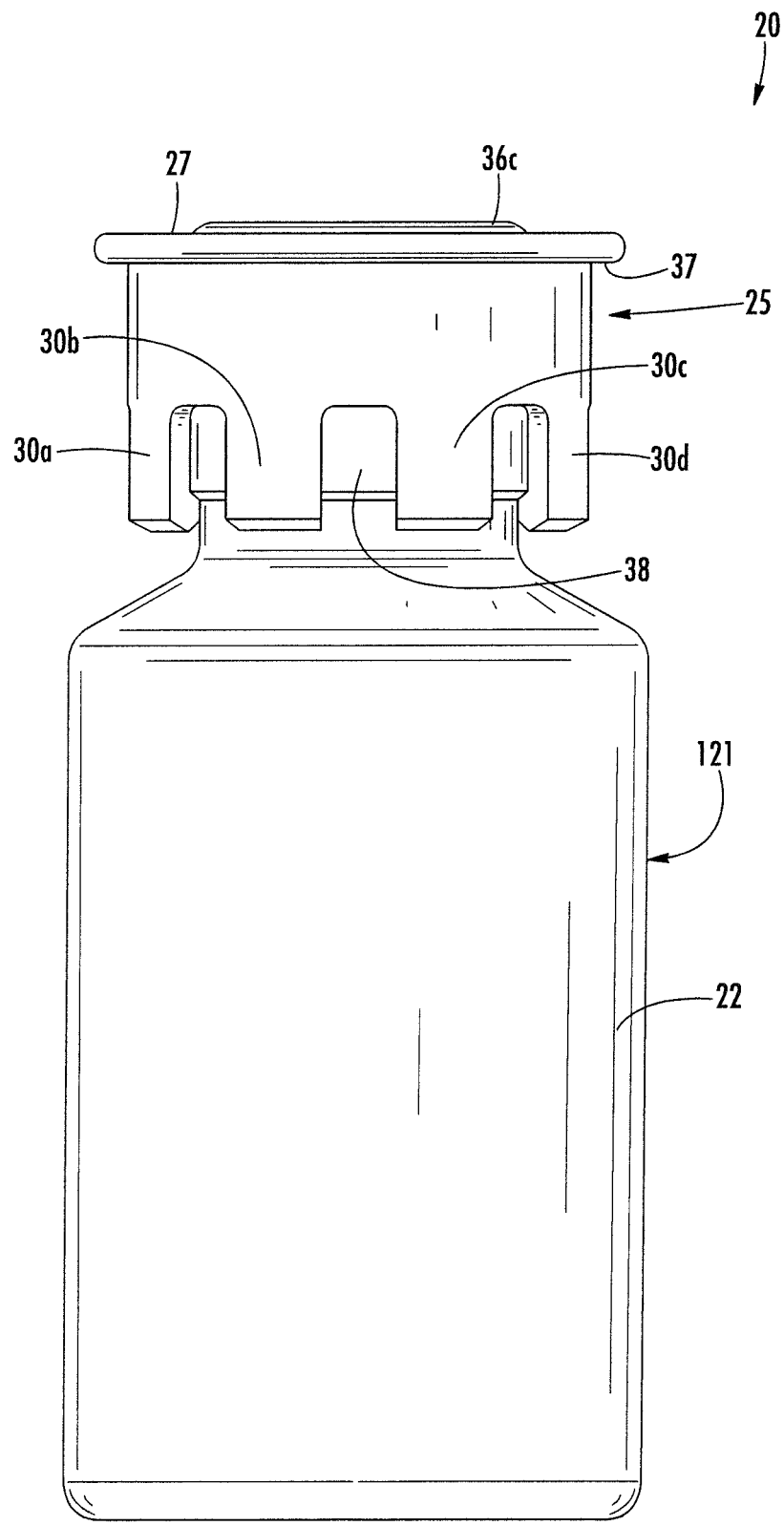
FIG. 2 is a schematic side view of the vial assembly from FIG. 1.
Figure 3:
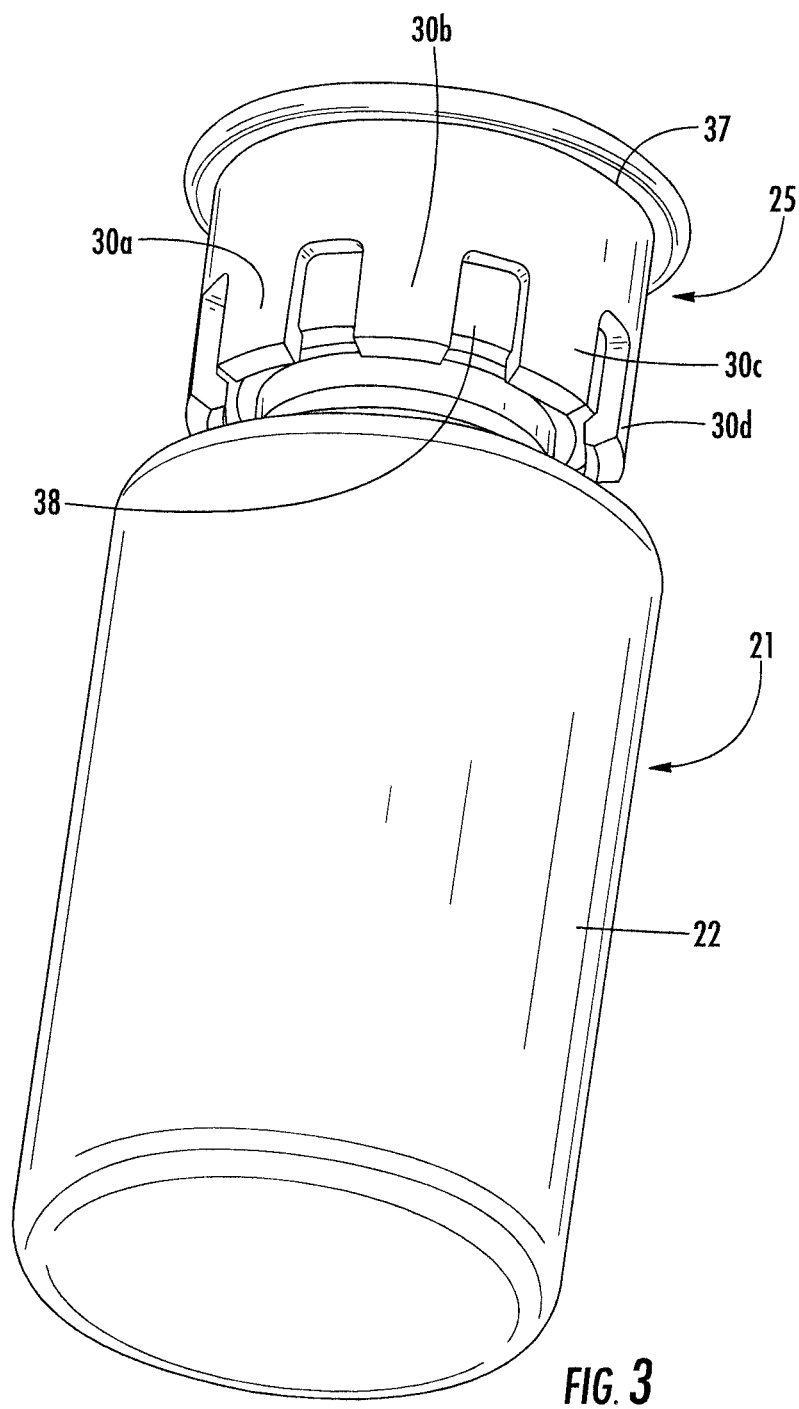
FIG. 3 is another schematic perspective view of the vial assembly from FIG. 1.

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout.

In theory, multi-dose vials provide substantial cost reduction benefits and waste reduction benefits to the user. Nevertheless, in typical multi-dose vials, there are several drawbacks for the institutional and home healthcare application. Most importantly, careful use procedures must be adhered to prevent contamination. Indeed, the Centers for Disease Control and Prevention provide guidelines for using the multi-dose vial safely.

Moreover, even when the guidelines are adhered to, the rubber access point (i.e. the access diaphragm) on the multi-dose vial can be contaminated from ambient atmosphere pollutants, such as dust, spray contamination, and splatter contamination. In some approaches, such as described in the "best practices for injection" from the National Institute for Health, the user is instructed to wipe the access diaphragm with an alcohol swab before use. Of course, this creates waste, and slows down the dosing process, and, is dependent on clinician compliance.

Referring to FIGS. 1-10, a vial assembly 20 according to the present disclosure is now described. The vial assembly 20 may provide an approach to the above noted drawbacks of the typical multi-dose vial.

The vial assembly 20 illustratively includes a vial 21 comprising a body 22 to hold a liquid material, and a neck 23 extending from the body. The vial 21 may comprise a multi-dose vial or a single-dose vial. The neck 23 illustratively includes a multi-use surface 24 configured to permit access to the liquid material stored within an interior of the body 22. As will be appreciated, the multi-use surface 24 comprises, for example, an access diaphragm. The multi-use surface 24 may comprise rubber, or polytetrafluoroethylene (PTFE). Also, the vial 21 comprises a durable material, such as glass, a plastic polymer, or an acrylic material. In the illustrated embodiment, the neck 23 comprises a crimp top 38 fitted over an open end of body 22, but other vial forms could be used, such as, for example, threaded top vials, and snap fit top vials.

The vial assembly 20 illustratively includes a cap 25 to be received by the neck 23 and to cover the multi-use surface 24. The cap 25 may comprise a plastic polymer material, for example. In some embodiments, the cap 25 could comprise a metallic material, or an acrylic material. Of course, these materials are merely exemplary, and other materials could be used.

The cap 25 illustratively includes a base 26 having a first major surface 27 (i.e. the upper surface), and a second major surface 28 opposite of the first major surface (i.e. the lower surface adjacent the body 22). The cap 25 illustratively includes a plurality of arms 30a-30h extending vertically and downward from the second major surface 28.

The cap 25 illustratively includes a rupturable reservoir 31 of disinfectant material carried by the base 26 between the first major surface 27 and the second major surface 28. The disinfectant material may comprise one or more of isopropyl alcohol, ethanol alcohol, aldehydes, oxidizing agents, peroxy, peroxo acids, phenolics, chlorine, iodine, or terpenes, for example. Of course, this listing is not exhaustive, and other disinfectant materials can be used. At least one of the first major surface 27 and the second major surface 28 is flexible so as to rupture the rupturable reservoir 31 when the cap 25 is received by the neck 23.

In particular, the second major surface 28 illustratively includes a plurality of flexible lateral supports 32a-32c defining gaps 33a-33c therebetween, i.e. the second major surface 28 is flexible. Of course, the gaps 33a-33c provide for the needed flexibility in the plurality of flexible lateral supports 32a-32c. Indeed, as perhaps best seen in FIG. 4, the plurality of flexible lateral supports 32a-32c are free moving at their distal ends. During application, the neck 23 of the vial 21 would apply upward pressure on the plurality of flexible lateral supports 32a-32c, which would compress and rupture the rupturable reservoir 31.

In the illustrated embodiment, each of the plurality of flexible lateral supports 32a-32c is circular segment-shaped. Of course, this shape is merely exemplary and other shapes could be used, such a rectangle shape.

Each of the plurality of flexible lateral supports 32a-32c comprises a distal protrusion 34a-34c extending transversely. Helpfully, the respective distal protrusion 34a-34c of the plurality of flexible lateral supports 32a-32c are positioned and aligned with the multi-use surface 24 when the cap 25 is positioned over the neck 23 of the vial 21. As discussed herein, the respective distal protrusion 34a-34c of the plurality of flexible lateral supports 32a-32c are configured to abrade and apply frictional force/pressure to the multi-use surface 24.

Additionally, the respective distal protrusion 34a-34c of the plurality of flexible lateral supports 32a-32c may have textured surfaces (e.g. a roughed surface). In other embodiments, each of the plurality of flexible lateral supports 32a-32c comprises a distal sponge for abrading the multi-use surface 24.

Figure 4:
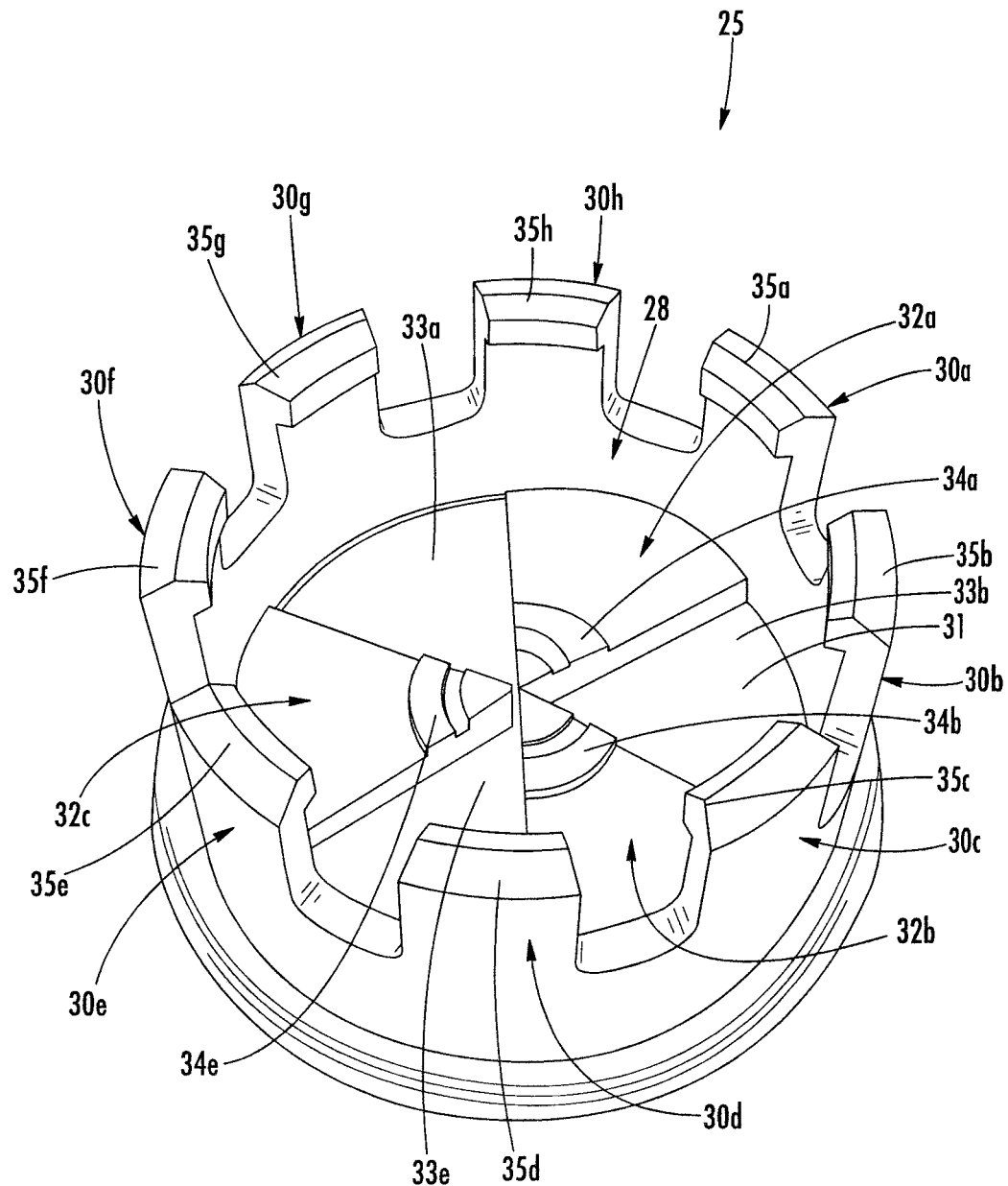
FIG. 4 is a schematic perspective view of the cap from the vial assembly from FIG. 1.
Figure 5:
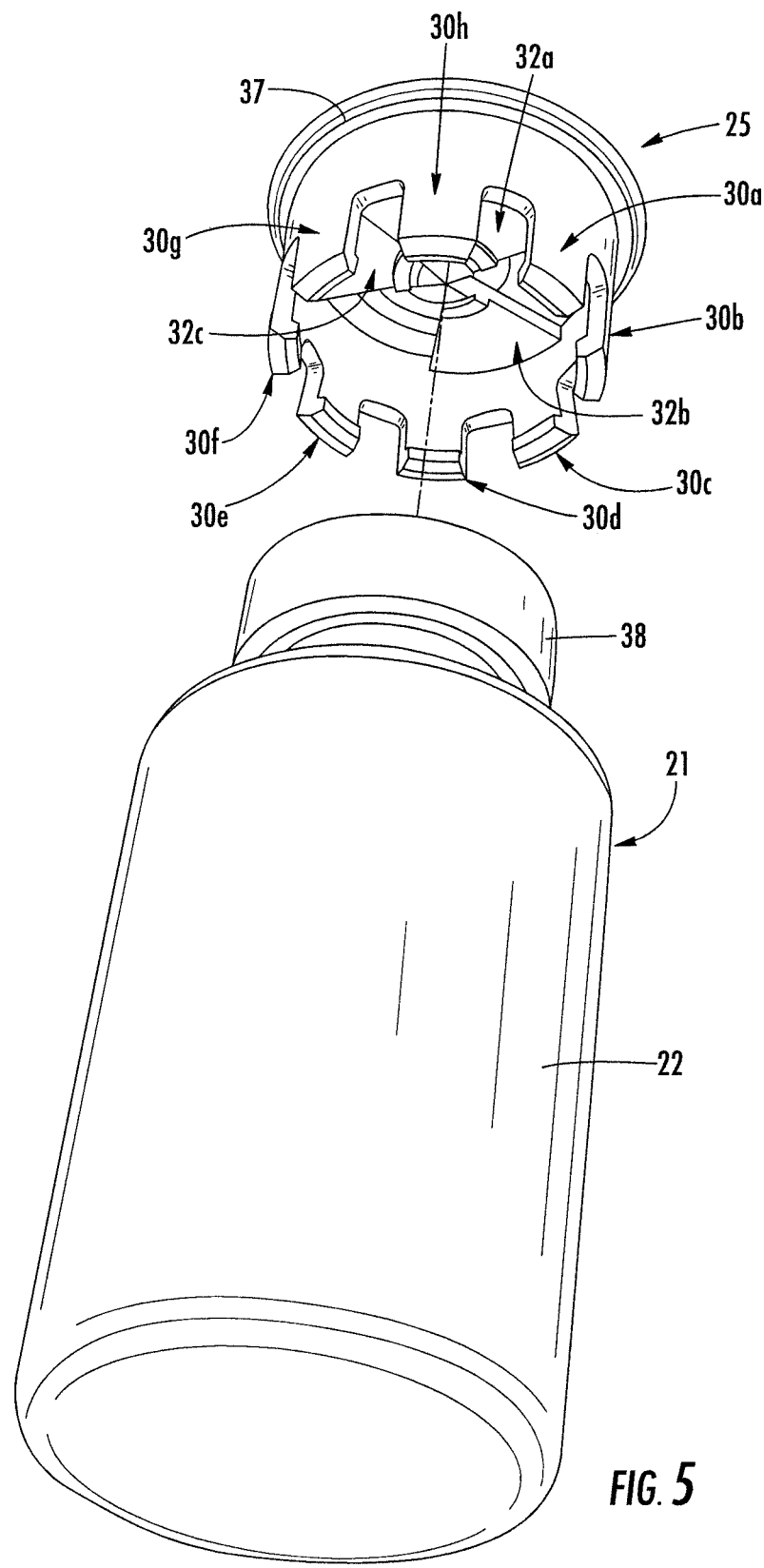
FIGS. 5 and 6 are schematic perspective views of the vial assembly from FIG. 1 with the cap separated.
Figure 6:
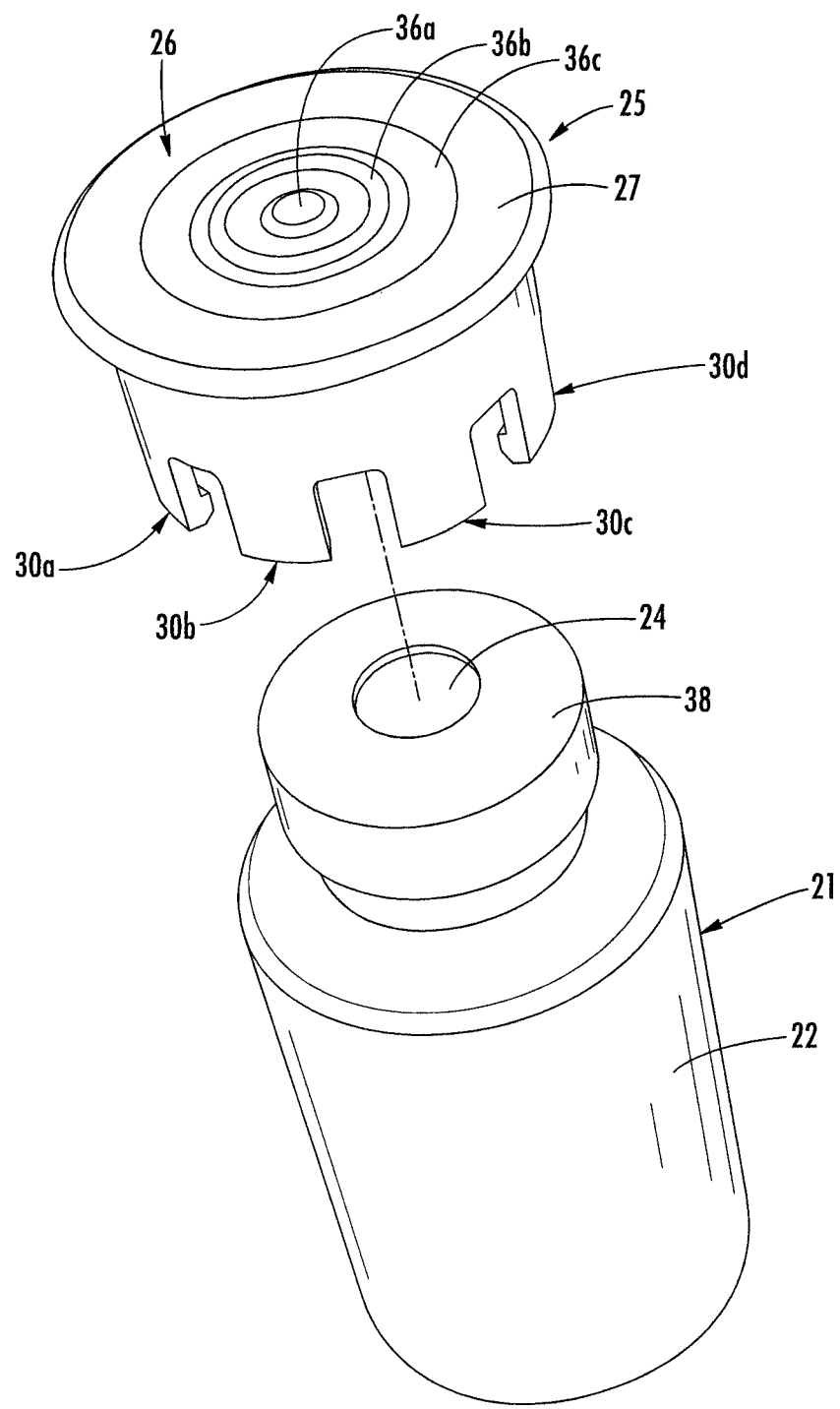

As perhaps best seen in FIG. 4, each of the respective distal protrusion 34a-34c of the plurality of flexible lateral supports 32a-32c has an inner radial portion, and an outer radial portion. The inner radial portion is circular segment-shaped. The outer radial portion is curved rectangle-shaped. The inner radial portion and the outer radial portion define a slot therebetween, which helpfully permits air flow to the multi-use surface 24 when the disinfectant material is being applied.

Figure 8:
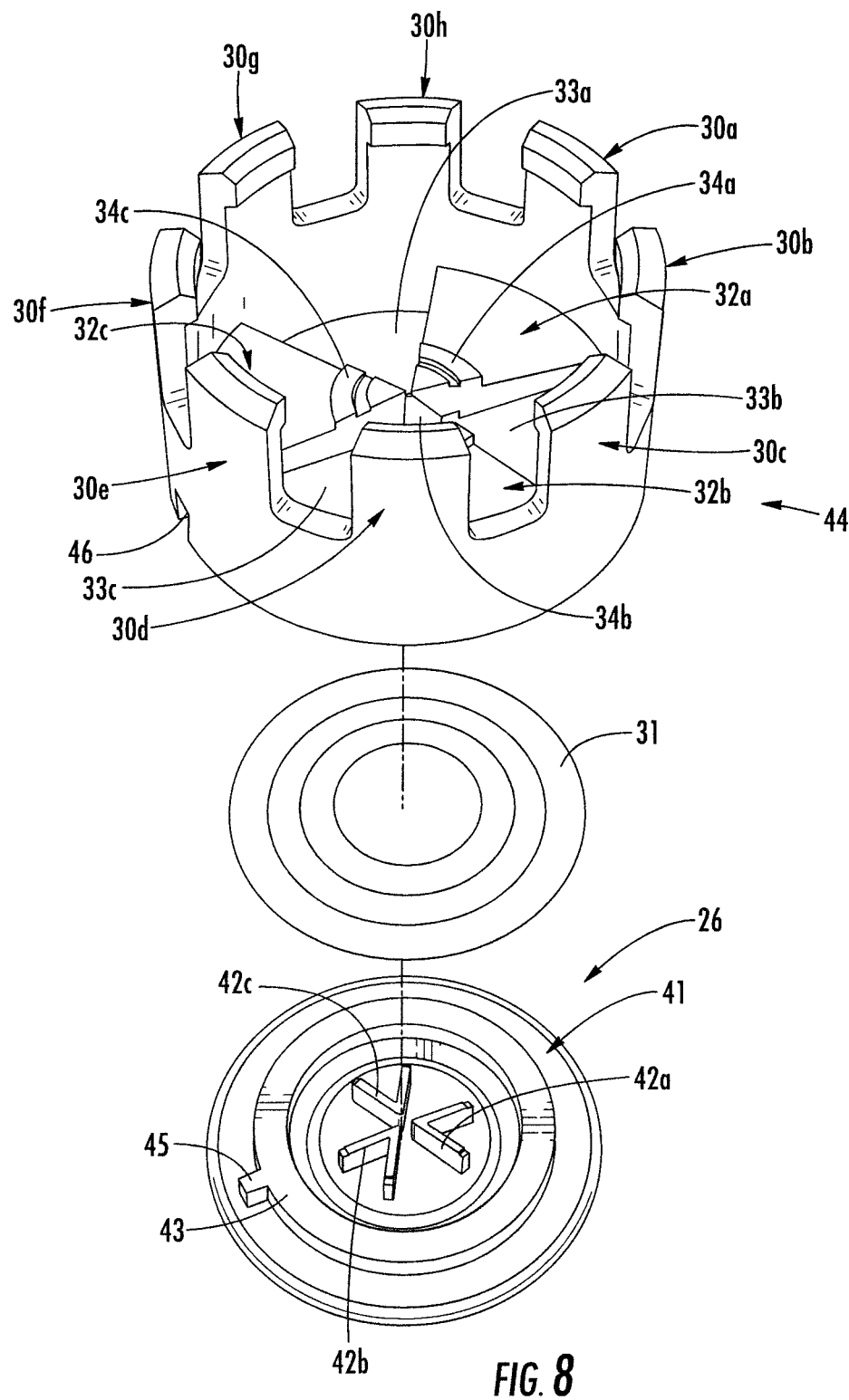
FIG. 8 is a schematic exploded view of the cap from the vial assembly from FIG. 1.
Figure 9:
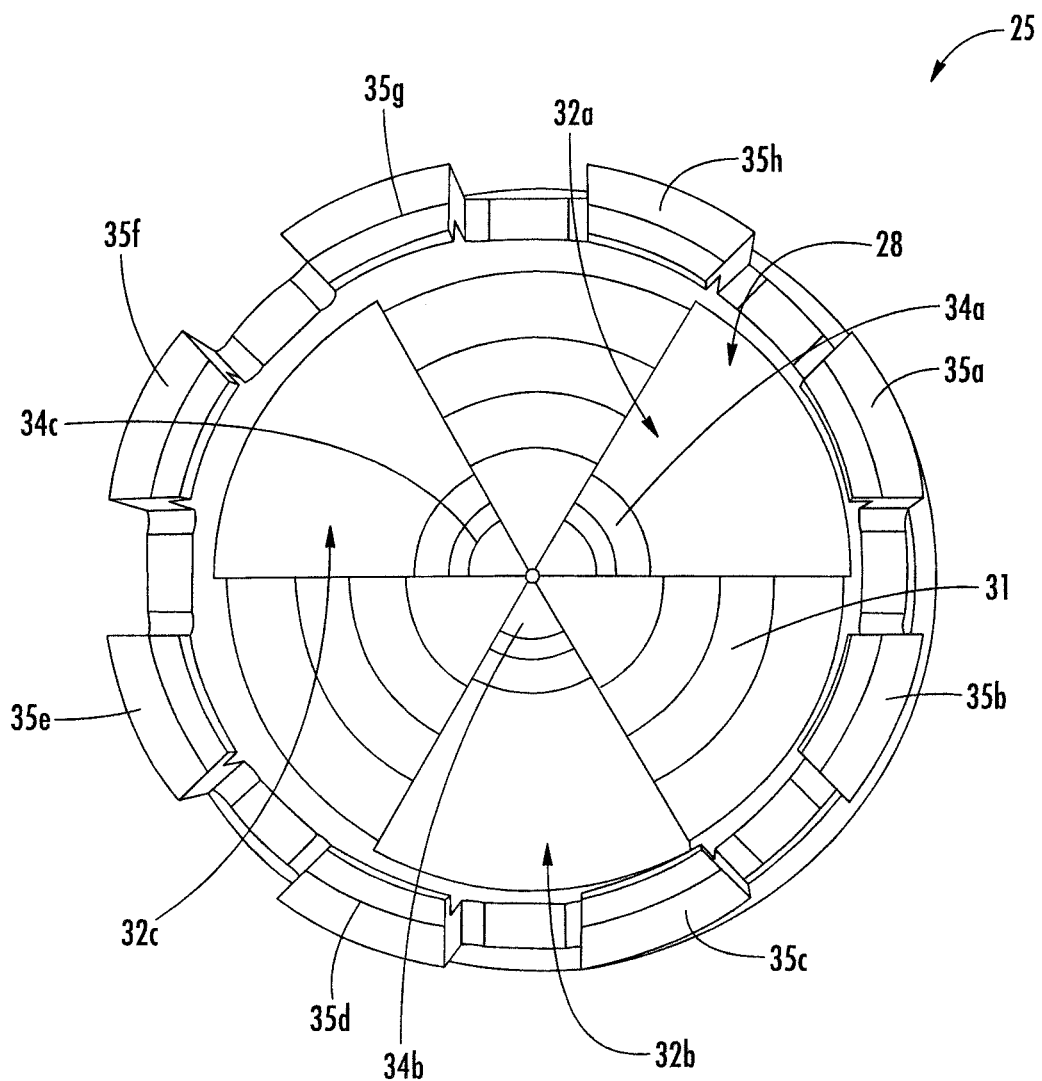
FIG. 9 is a schematic bottom view of the cap from the vial assembly from FIG. 1.
Figure 10:
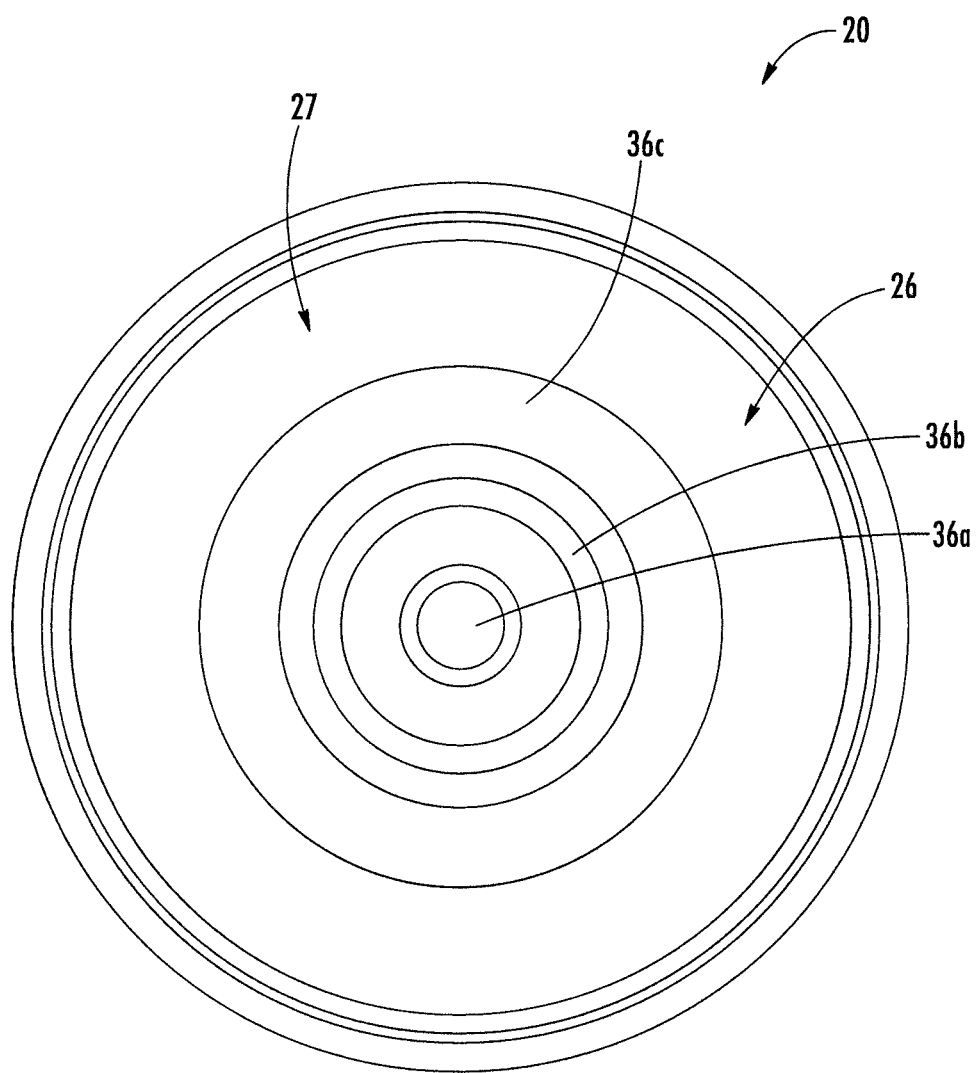
FIG. 10 is a schematic top view of the cap from the vial assembly from FIG. 1.

Additionally, as perhaps best seen in FIG. 8, each of the plurality of arms 30a-30h illustratively includes an L-shaped distal end portion 35a-35h for abutting and retaining the neck 23. Each of the plurality of arms 30a-30h illustratively extends substantially perpendicular (i.e. ±10 degrees from normal 90°) to the second major surface 28. Helpfully, when a new cap 25 is applied to the vial 21, the cap is securely retained to the vial.

In some embodiments, the plurality of arms 30a-30h are omitted and replaced with cylinder-shaped shroud (i.e. a solid annular wall). In other embodiments, the inner radial wall of the solid annular wall comprises threading to be received by opposing threading on the neck 23 of the vial 21.

In some embodiments, the rupturable reservoir 31 may comprise a foil material body carrying the disinfectant material therein. In other embodiments, the rupturable reservoir 31 may comprise clear, flexible plastic. The material of the rupturable reservoir 31 needs to be puncturable, but resilient enough to survive assembly of the cap 25 and storage before use.

The base 26 illustratively includes a circle-shaped base. Of course, the circle shape is merely exemplary, and the base could have other forms, such as a square shape.

The first major surface 27 illustratively includes a plurality of ridges 36a-36c. Helpfully, the plurality of ridges 36a-36c may enable sure grasping of the cap 25 when being fitted over the vial 21, which prevents damage to the vial 21.

Figure 7:
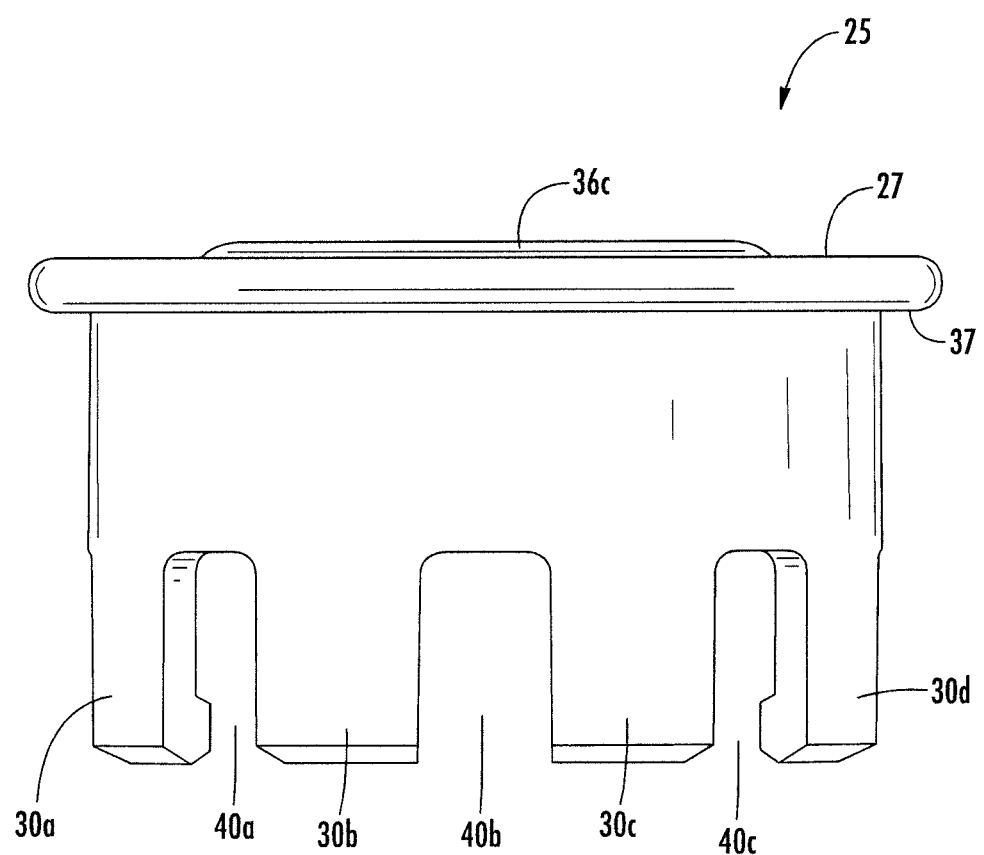
FIG. 7 is a schematic side view of the cap from the vial assembly from FIG. 1.

Also, as perhaps best seen in FIG. 7, the base 26 illustratively includes a flanged annular edge 37, which also aids for sure removal of the cap 25 from the vial 21. The plurality of arms 30a-30h define respective slots 40a-40c therebetween. The respective slots 40a-40c permit sufficient outward flexibility to permit the plurality of arms 30a-30h to flex outward and snap fit against the neck 23 of the vial 21. Also, the respective slots 40a-40c permit sufficient airflow for the disinfectant material to dry on the multi-use surface 24.

As perhaps best seen in FIG. 8, the base 26 illustratively includes an upper housing 41 defining the first major surface 27 (not shown in this figure), and a lower housing 44. The upper housing 41 and the lower housing 44 interlock together to carry the rupturable reservoir 31 therebetween.

The upper housing 41 illustratively includes an interlocking interface opposite the first major surface 27 and comprising an annular ridge 43, and a plurality of protrusions 42a-42c extending from within the annular ridge and configured to abut the rupturable reservoir 31. In the illustrated embodiment, the plurality of protrusions 42a-42c are each V-shaped, with vertices being adjacent. In other embodiments, the plurality of protrusions 42a-42c may have other shapes, such as a circle shape or an elongate rectangle shape. The annular ridge 43 comprises a tab 45 extending radially outward. Of course, in other embodiments, multiple tabs can be included.

The lower housing 44 illustratively includes a substantially cylinder-shaped body (i.e. an annular wall), which is to fit into the interlocking interface of the upper housing 41. The lower housing 44 comprises the plurality of arms 30a-30h at a first end, and the substantially cylinder-shaped body at the second end opposite to the first end. The substantially cylinder-shaped body defines a peripheral slot 46 configured to fit the tab 45 of the upper housing 41 when assembled.

In other words, in the illustrated embodiment the base 26 of cap 25 is assembled/manufactured via an interface fit. In other embodiments, the upper housing 41 and lower housing 44 may be coupled together using an adhesive or plastic heat bonding (i.e. plastic welding). In yet other embodiments, the cap 25 may be integrally formed as one-piece surrounding the rupturable reservoir 31, for example, an injection molding process.

In some embodiments, the first major surface 27 of the base 26 of the cap 25 is additionally or alternatively, (with regards to the second major surface 28 being flexible) comprised of a flexible material. In these embodiments, the user applies pressured downward on first major surface 27, and the first major surface indents and ruptures the rupturable reservoir 31. In this embodiment, the plurality of flexible lateral supports 32a-32c may or may not be flexible. When the plurality of flexible lateral supports 32a-32c is not flexible, they provide only an abrasion function for the disinfectant material.

Another aspect is directed to a method for making a cap 25 to be used with a vial 21. The cap 25 includes a body 22 to hold a liquid material, and a neck 23 extending from the body. The neck 23 includes a multi-use surface 24 configured to permit access to the liquid material. The cap 25 is to be received by the neck 23 and to cover the multi-use surface 24. The method comprises forming a base 26 having a first major surface 27, and a second major surface 28 opposite of the first major surface, forming a plurality of arms 30a-30h extending from the second major surface, and positioning a rupturable reservoir 31 of disinfectant material carried by the base between the first major surface and the second major surface. The second major surface 28 is flexible so as to rupture the rupturable reservoir 31 when the cap 25 is received by the neck 23.

Yet another aspect is directed to a method for using a vial assembly 20. The vial assembly 20 includes a vial 21 comprising a body 22 to hold a liquid material, and a neck 23 extending from the body, the neck comprising a multi-use surface 24 configured to permit access to the liquid material. The vial assembly 20 includes a cap 25 to be received by the neck 23 and to cover the multi-use surface 24. The vial assembly 20 includes a base 26 having a first major surface 27, and a second major surface 28 opposite of the first major surface, a plurality of arms 30a-30h extending from the second major surface, and a rupturable reservoir 31 of disinfectant material carried by the base between the first major surface and the second major surface. The method includes extracting a dose from the vial 21 (e.g. using a syringe), and positioning the cap 25 over the vial 21 so that the second major surface 28, which is flexible, ruptures the rupturable reservoir 31.

Advantageously, when a dose is extracted from the vial 21 (in multi-dose embodiments), the multi-dose vial is returned to storage with the cap 25. On the next use, the user would apply pressure from first major surface 27, and the plurality of flexible lateral supports 32a-32c would puncture the rupturable reservoir 31. Moreover, the distal protrusions 34a-34c of the plurality of flexible lateral supports 32a-32c would abrade the multi-use surface 24 and work the disinfectant material into the multi-use surface 24. After use, the cap 25 would be disposed of, and a new cap would be applied to the vial 21 after the next dose extraction.

In some applications, the cap 25 is intended for single use. In particular, the rupturable reservoir 31 can dispense the disinfectant material only once. Nevertheless, in other embodiments, the rupturable reservoir 31 may dispense the disinfectant material multiple times. For example, the rupturable reservoir 31 may comprise a porous body (e.g. a sponge) within the breakable seal, and each time the second major surface 28 is flexed upward, more disinfectant material is dispensed.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

That which is claimed is:

1. A vial assembly comprising:
   a vial comprising a body to hold a liquid material, and a neck extending from said body, said neck comprising a multi-use surface configured to permit access to the liquid material; and
   a cap to be received by said neck and to cover said multi-use surface, said cap comprising
   a base having a first major surface, and a second major surface opposite of said first major surface,
   a plurality of arms extending from said second major surface, and
   a rupturable reservoir of disinfectant material carried by said base between said first major surface and said second major surface,
   at least one of said first major surface and said second major surface being flexible so as to rupture said rupturable reservoir when said cap is received by said neck.

2. The vial assembly of claim 1 wherein said second major surface comprises a plurality of flexible lateral supports defining gaps therebetween.

3. The vial assembly of claim 2 wherein each of said plurality of flexible lateral supports comprises a distal protrusion extending transversely.

4. The vial assembly of claim 2 wherein each of said plurality of flexible lateral supports is circular segment-shaped.

5. The vial assembly of claim 1 wherein each of said plurality of arms comprises an L-shaped distal end portion for abutting and retaining said neck.

6. The vial assembly of claim 1 wherein each of said plurality of arms extends substantially perpendicular to said second major surface.

7. The vial assembly of claim 1 wherein said rupturable reservoir comprises a foil material body carrying said disinfectant material therein.

8. The vial assembly of claim 1 wherein said first major surface comprises a plurality of ridges.

9. The vial assembly of claim 1 wherein said base comprises a circle-shaped base, and comprises a flanged annular edge.

10. A cap to be used with a vial comprising a body to hold a liquid material, and a neck extending from the body, the neck comprising a multi-use surface configured to permit access to the liquid material, the cap to be received by the neck and to cover the multi-use surface, the cap comprising
a base having a first major surface, and a second major surface opposite of said first major surface;
a plurality of arms extending from said second major surface; and
a rupturable reservoir of disinfectant material carried by said base between said first major surface and said second major surface;
at least one of said first major surface and said second major surface being flexible so as to rupture said rupturable reservoir when the cap is received by the neck.

11. The cap of claim 10 wherein said second major surface comprises a plurality of flexible lateral supports defining gaps therebetween.

12. The cap of claim 11 wherein each of said plurality of flexible lateral supports comprises a distal protrusion extending transversely.

13. The cap of claim 11 wherein each of said plurality of flexible lateral supports is circular segment-shaped.

14. The cap of claim 10 wherein each of said plurality of arms comprises an L-shaped distal end portion for abutting and retaining said neck.

15. The cap of claim 10 wherein each of said plurality of arms extends substantially perpendicular to said second major surface.

16. The cap of claim 10 wherein said rupturable reservoir comprises a foil material body carrying said disinfectant material therein.

17. A method for making a cap to be used with a vial comprising a body to hold a liquid material, and a neck extending from the body, the neck comprising a multi-use surface configured to permit access to the liquid material, the cap to be received by the neck and to cover the multi-use surface, the method comprising
forming a base having a first major surface, and a second major surface opposite of the first major surface;
forming a plurality of arms extending from the second major surface; and
positioning a rupturable reservoir of disinfectant material carried by the base between the first major surface and the second major surface;
at least one of the first major surface and the second major surface being flexible so as to rupture the rupturable reservoir when the cap is received by the neck.

18. The method of claim 17 wherein the second major surface comprises a plurality of flexible lateral supports defining gaps therebetween.

19. The method of claim 18 wherein each of the plurality of flexible lateral supports comprises a distal protrusion extending transversely.

20. The method of claim 18 wherein each of the plurality of flexible lateral supports is circular segment-shaped.

* * * * *